United States Patent
Corley

Patent Number: 5,340,890
Date of Patent: Aug. 23, 1994

[54] CYCLOBUTENE ANHYDRIDE-CURED EPOXY RESIN COMPOSITION

[75] Inventor: Larry S. Corley, Houston, Tex.

[73] Assignee: Shell Oil Company, Houston, Tex.

[21] Appl. No.: 10,128

[22] Filed: Jan. 28, 1993

[51] Int. Cl.$^5$ .................. C08G 59/40; C08G 59/42; C08G 65/00

[52] U.S. Cl. .................. 525/530; 525/422; 525/533; 528/90; 528/112; 528/113; 528/114; 528/115; 528/220; 528/313; 528/322; 528/365

[58] Field of Search .................. 528/90, 112, 113–115, 528/220, 313, 322, 365; 525/422, 530, 533

[56] References Cited

U.S. PATENT DOCUMENTS

| | | | |
|---|---|---|---|
| 2,890,204 | 6/1959 | Delmonte | 525/524 |
| 2,967,843 | 1/1961 | Delmonte et al. | 528/112 |
| 3,725,345 | 4/1973 | Bargain | 528/113 |
| 3,730,948 | 5/1973 | Akiyama et al. | 528/113 |
| 4,540,763 | 9/1985 | Kirchhoff | 526/281 |
| 4,927,907 | 5/1990 | Corley | 528/322 |
| 4,973,636 | 11/1990 | Corley | 526/262 |
| 5,147,953 | 9/1992 | Corley | 526/262 |

OTHER PUBLICATIONS

Blomquist et al., "1,2-Dimethylenecyclobutane," J. Am. Chem. Soc. 77, 1806–9 (1955).

*Primary Examiner*—Frederick Krass

[57] ABSTRACT

An epoxy resin composition containing an anhydride-functional cyclobutene which can be represented by the formula

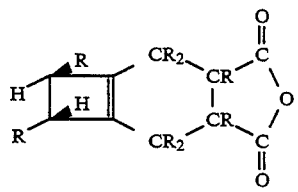

in which each R is independently selected from hydrogen, $C_{1-10}$ alkyl, aryl, halide and $C_{1-10}$ heteroatomic.

11 Claims, No Drawings

CYCLOBUTENE ANHYDRIDE-CURED EPOXY RESIN COMPOSITION

BACKGROUND OF THE INVENTION

This invention relates to anhydride-functional compositions of matter. In one embodiment, the invention relates to new anhydride curing agents for epoxy resins.

Standard monoanhydride curing agents for epoxy resins, such as phthalic anhydride, methyl tetrahydrophthalic anhydride and methyl hexahydrophthalic anhydride, give resin/curing agent mixtures which are easily processed but cure to castings with low Tg values (usually below 200° C.) when used with standard commercial difunctional liquid epoxy resins based on bisphenol A. Dianhydrides such as benzophenonetetracarboxylic dianhydride (BTDA) and pyromellitic dianhydride (PMDA) give cured epoxy resins with high Tg values but short "processing windows" and liquid processing of such epoxy systems is difficult because of the high melting points of the anhydrides (225° C. for BTDA and 286° C. for PMDA, for example). The epoxy resin containing the powdered dianhydride has to be heated to very high temperatures in order to dissolve the powder, and in many cases it is difficult to dissolve the dianhydride completely before the system gels.

It is therefore an object of the invention to provide epoxy resin compositions which have good processing characteristics and high cured Tg.

SUMMARY OF THE INVENTION

According to the invention, a composition of matter is provided which comprises (a) an epoxy resin and (b) an anhydride-functional compound according to the structural formula:

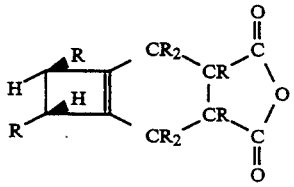

in which each R is selected independently from hydrogen, $C_{1\text{-}10}$ alkyl, aryl, halide, and $C_{1\text{-}10}$ hetero-interrupted (alkyl or aryl) such as alkoxy, aryloxy, alkylthio, arylthio and dialkylamino.

DETAILED DESCRIPTION OF THE INVENTION

The invention is a composition of matter containing an epoxy resin and a cyclic anhydride of the formula:

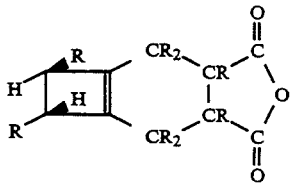

in which each R is selected independently from hydrogen, $C_{1\text{-}10}$ alkyl, aryl, halide, and $C_{1\text{-}10}$ hetero-interrupted (alkyl or aryl) such as alkoxy, aryloxy, alkylthio, arylthio and dialkylamino. Preferred cyclic anhydrides are those in which each R is selected independently from hydrogen and methyl, as in bicyclo[4.2.0]oct-1(6)-ene-3,4-dicarboxylic anhydride (BODA)

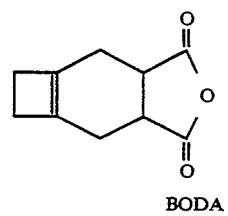

BODA and 3-methylbicyclo[4.2.0]oct-1 (6)-ene-3,4-dicarboxylic anhydride (MBODA)

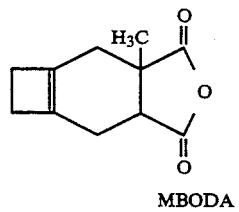

MBODA

The Dieis-Alder adducts of 1,2-dimethylenecyclobutane with maleic anhydride or substituted maleic anhydrides (such as citraconic anhydride) are particularly preferred.

The anhydride-functional cyclobutene compound can be synthesized by various procedures including the Dieis-Alder reaction of 1,2-dimethylenecyclobutane (or a molecule containing this moiety) with an anhydride containing a dienophilic group, such as maleic anhydride or substituted maleic anhydrides. In general, the anhydride-functional cyclobutene compound can be prepared by contacting a 1,2-dialkylidenecyclobutane with an anhydride-functional dienophile in an optional organic solvent at a temperature within the range of about 0° to about 100° C., followed by removal of unconsumed reactants and solvent. The product can be purified by recrystallization from an organic solvent such as cyclohexane. Preparation of anhydride-functional cyclobutene compounds is illustrated in Examples 2 and 3 herein.

The anhydride-functional cyclobutene compounds are present in the invention compositions in an amount effective to cure the epoxy resin component, generally an amount within the range of about 0.5 to about 1.2 moles per mole of the epoxy resin. They can be blended with other monoanhydrides such as methyl tetrahydrophthalic anhydride to provide systems of lower viscosity (and generally higher cured toughness) than those in which the anhydride-functional cyclobutene compound is used as the sole curing agent. Alternatively, they may be used in curing agent blends with an anhydride which contains a dienophilic group, such as maleic or itaconic anhydride. At elevated temperature, the cyclobutene ring will open to a diene which will then react with the dienophilic group to produce a densely-crosslinked structure. Similarly, molecules containing two or more dienophilic groups, such as bis-maleimides and di- and triacrylates, can react with the diene groups produced by cyclobutene ring opening and can co-crosslink with an epoxy system cured with an anhydride-functional cyclobutene compound. They may impart improved properties to such systems, such as greater heat resistance and toughness in the case of bismaleimides and lower viscosity in the case of di- and triacrylates. The diene groups formed by cyclobutene ring opening are also susceptible to radical polymerization, enabling radically polymerizable monomers used as diluents (such as styrene or methacrylates) to become chemically bonded to the crosslinked epoxy network.

The epoxy resin component of the invention composition includes solid or liquid glycidyl ethers having, on the average, more than about 1.75 vicinal epoxide groups per molecule, including diglycidyl ethers of bisphenol A and bisphenol F, for example.

The invention compositions can include various optional additives including cure accelerators such as imidazoles, radical polymerization inhibitors such as phenothiazine, and defoaming agents such as acrylic oligomers.

The invention compositions are useful as matrices for high-temperature composites with glass, graphite or other fibers prepared by such techniques as prepreg techniques, filament winding, pultrusion and resin transfer molding. They can also be used in coating, adhesive and electrical encapsulation formulations.

was also introduced into the loop just upstream from the recirculation pump.

The system was first purged with nitrogen. The power to the fluidized bed was turned on and its temperature was brought to 450°–470° C. Allene was introduced into the system from the allene cylinder at a rate of 80–100 g/hr. The allene supply from the cylinder was shut off two to three hours before the end of a dimerization run in order that the allene present in the system could be used up, with little allene remaining in the reservoir at the end. At the end of the day, the power to the fluidized bed was turned off, the system was allowed to cool, and the accumulated dimer was poured into a bottle and weighed. Approximately 3 g of phenothiazine was added per kilogram of dimer to inhibit polymerization of the 1,2-dimethylenecyclobutane. The crude dimer was then analyzed by gas chromatography for peaks corresponding to two allene dimers, 1,2-dimethylenecyclobutane (1,2-DMCB) and 1,3-dimethylenecyclobutene (1,3-DMCB), and a component shown by mass spectrometry to have a molecular formula of $C_9H_{12}$ (an allene trimer). Data from seven hot tube reaction runs are shown in Table 1.

TABLE 1

| Reaction # | Reaction time, hr. | Allene used, g | Crude dimer produced, g | Crude yield, % | GC analysis | | |
|---|---|---|---|---|---|---|---|
| | | | | | 1,3-DMCB, % | 1,2-DMCB, % | $C_9H_{12}$ peak, % |
| 1 | 8.0 | 558 | 443 | 79.4 | 8.4 | 67.0 | 15.0 |
| 2 | 15.8 | 1197 | 881 | 73.6 | 8.1 | 75.0 | 11.0 |
| 3 | 11.3 | 862 | 753 | 87.3 | 8.3 | 73.4 | 11.4 |
| 4 | 11.2 | 824 | 647 | 78.5 | 8.3 | 71.6 | 14.0 |
| 5 | 11.8 | 932 | 806 | 86.5 | 8.5 | 68.7 | 15.4 |
| 6 | 11.4 | 909 | 746 | 82.1 | 8.4 | 68.0 | 16.2 |
| 7 | 11.0 | 872 | 724 | 83.0 | 8.5 | 69.0 | 15.7 |

EXAMPLE 1

Preparation of 1,2-Dimethylenecyclobutane. A recirculating apparatus for the thermal dimerization of allene was designed as follows. The heated reactor was a bank of approximately 110 segments (each about 30 cm long) of stainless steel tubing 1.27 cm in outside diameter. The segments were arranged vertically in series and connected to one another by U-shaped stainless steel connectors to which they were welded. The volume of the heated portion of the reactor was about 3.4 liters. The bank of tubes was immersed in a fluidized bed of aluminum oxide particles. Thermocouples wedged between the connectors of the reactor at various points allowed one to monitor the wall temperature of different segments of the reactor.

Downstream from the reactor was a cold trap containing a cooling fluid at approximately −65° C. above a flask which functioned as a gas-liquid separator. Downstream from the first trap was a second trap filled with dry ice in dichloromethane, guarding the outlet to the system (through an oil bubbler) to condense any allene which otherwise could have escaped from the system. Condensed allene from this second trap fell into the gas-liquid separator. The condensed material (allene dimers and some of the allene) from the traps fell to the bottom of the separator and then flowed through a fluoropolymer tube into a reservoir for liquid allene and allene dimers. Sufficient heat was applied to this reservoir to keep the allene boiling gently. The allene not condensed by the cold traps was combined with that evaporating from the reservoir. This stream of recovered allene was passed through a filter into a diaphragm pump which recirculated the allene back into the hot tube. A makeup stream of fresh allene from a cylinder The products of the seven runs in Table I were flash-distilled under vacuum to remove tars and were subsequently distilled under reduced pressure in 2.54 cm Oldershaw columns with 30 plates. The resulting distilled fractions and similarly-obtained DMCB cuts were used in the following examples.

EXAMPLE 2

Preparation of Bicyclo[4.2.0]oct-1(6)-ene-3,4-dicarboxylic Anhydride (BODA). Into a 500-mL, single-neck round bottom glass flask containing a magnetic stirring bar were weighed 76.49 grams (0.78 moles) of maleic anhydride, 0.20 grams of phenothiazine (antioxidant and radical polymerization inhibitor) and 200 grams of dichloromethane. The flask was then fitted with a three-neck adapter to which was attached a thermometer, a condenser and a 250-mL addition funnel. To the funnel was added 91.66 grams of a distilled dimethylenecyclobutane (DMCB) cut containing 69.6% (by GC) 1,2-isomer (63.76 grams, or 0.795 moles, of 1,2-dimethylenecyclobutane). The flask was purged with dry nitrogen. The DMCB was then added dropwise to the maleic anhydride solution with stirring. Refluxing of the dichloromethane kept the temperature of the flask content below approximately 50° C. during the DMCB addition. When the DMCB addition was complete, the mixture was allowed to stand for three days at room temperature to complete the reaction. Solvent and unreacted volatiles were removed at 60° C. at a pressure which was gradually decreased from atmospheric to 20 Pa; the crude product was finally held at 60° C. and 20 Pa for 2 hours to complete the removal of these materials. The crude yield was 136.2 grams (98%). 133 grams of the product was recrystallized from 250 grams of cyclohexane with strong stirring. Yield of recrystallized BODA was 128 grams (94%). Melting point was 81°–83° C. The melting point reported in the literature (A.T. Blomquist and J.A. Verdol, *J. Am. Chem. Soc.*, 77, 1806–9 (1955)) was 77°–78° C.

EXAMPLE 3

Preparation of 3-Methylbicyclo[4.2.0]oct-1(6)-ene-3,4,-Dicarboxylic Anhydride (MBODA). Into a 500-mL, single-neck round bottom glass flask containing a magnetic stirring bar was weighed 96.62 grams (0.862 moles) of citraconic anhydride. The flask was then fitted with a three-neck adapter to which was attached a thermometer, a condenser and a 250-mL addition funnel. To the funnel was added 86.0 grams of a distilled dimethylenecyclobutane (DMCB) cut containing 90.2% (by GC) 1,2-isomer (77.6 grams, or 0.968 moles, of 1,2-dimethylenecyclobutane). The flask was purged with dry nitrogen. The DMCB was then added dropwise to the citraconic anhydride with stirring. No temperature increase due to reaction exotherm was evident. When the DMCB addition was complete, the mixture was allowed to stand for 53 days at room temperature to complete the reaction. At the end of this period, gas chromatography revealed that the peak corresponding to unreacted citraconic anhydride had essentially disappeared. The product was then dissolved in dichloromethane and filtered to remove insoluble gelatinous material. Dichloromethane and unreacted volatiles were removed at 60° C. on a rotary evaporator to yield a crystalline product. The crude yield was 156.18 grams (94%). 152 g of product was then recrystallized from 165 grams of cyclohexane with strong stirring. Yield of recrystallized MBODA was 132.17 grams (80%). Melting point was 64°–68° C. The $^1$H and $^{13}$C NMR spectra of the product were consistent with the following structure; no impurities were seen in the product by NMR except for a small amount of cyclohexane.

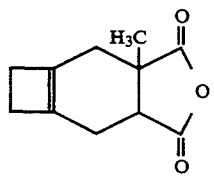

EXAMPLE 4

Comparison of BODA and MBODA with Various Commercially-Available Monoanhydrides and dianhydrides as Epoxy Resin Curing Agents. Nine mixtures (mixtures 1–9 in Table 2 below) were prepared as follows. To 250-mL filtering flasks were added the amounts shown of EPON® Resin 828, BODA, MBODA, four control anhydrides [methyl tetrahydrophthalic anhydride (MTHPA) (Lindride 6), Nadic methyl anhydride (NMA) (Aldrich), Epiclon B-4400 (an adduct of piperylene with two moles of maleic anhydride, sold by Dainippon Ink), and benzophenonetetracarboxylic dianhydride (BTDA) (Aldrich)], 2-ethyl-4-methylimidazole (Air Products EMI-24, an accelerator for the epoxy-anhydride reaction) a 60% solution of potassium 2-ethylhexanoate in a glycol mixture (Air Products DABCO T-45, another accelerator for the epoxy-anhydride reaction), phenothiazine (an antioxidant and inhibitor of radical polymerization) and Monsanto PC-1344 defoamer (an acrylic oligomer, added to prevent excessive foaming during degassing and to enable the preparation of void-free castings).

The mixtures were stirred until homogeneous, at room temperature for the mixtures using the MTHPA and NMA (which are liquid at room temperature) and with the flasks in an 80° C. or 90° C. oil bath for the mixtures containing the BODA and MBODA (which are solid at room temperature) and in a 130° C. oil bath for the mixtures containing the Epiclon B-4400 and BTDA. After homogeneous mixtures were obtained, the mixtures were degassed under vacuum, with stirring by a magnetic stirring bar, until bubbling stopped. Mixtures #1, 2, 4, 5, 6 and 7 were then poured into preheated molds which consisted of two sheets of glass ⅛" (3.18 mm) thick clamped together and separated by a polytetrafluoroethylene spacer of the same thickness. Mixture #3 containing MBODA and mixture #8 containing Epiclon B-4400 were then poured into a preheated two-piece rectangular stainless steel mold with a ⅛" (3.18 mm) thick cavity, with the mold parts separated by a gas tight silicone rubber gasket such that the mold could be pressurized during cure. (Mixture #9 containing BTDA, under the processing conditions used, increased in viscosity so rapidly during degassing that it became too viscous to pour into a mold and hence a casting was not made.) The molds were then placed into an oven, and the stainless steel molds were pressurized with nitrogen to 750 kPa (~95 psig). The mixtures were cured for 1 hour at 120° C., followed by ramping linearly to 260° C. over a period of 3.5 hours and then holding for 1 hour at 260° C. Cured properties of the castings are shown in Table 2.

Gel time of a number of the uncured systems was measured on a hot plate at the temperatures indicated in Table 2. The gel time was taken as the time at which a "stringy" fiber could no longer be pulled with a tongue depressor from the pool of resin (1–2 grams) on the hot plate surface. For the systems liquid at room temperature, Ubbelohde viscosity was determined at 25° C. For some of the systems which were pastes or highly viscous liquids at room temperature, viscosity was measured with a rotating viscometer under continuously increasing temperature and the temperature was recorded at which the viscosity dropped to 1 Pa.s. These uncured properties are also shown in Table 2.

One can see from Table 2 that the use of the monoanhydrides BODA and MBODA yielded a dramatic increase in glass transition temperature of the cured epoxy relative to the control monoanhydrides (MTHPA and NMA). Glass transition temperature of the BODA- and MBODA-cured epoxy was similar to that of the epoxy cured with the dianhydride Epiclon B-4400, which melts at 173° C. compared to 81°–83° C. for the BODA and 64°–68° C. for the MBODA. Absorption of methyl ethyl ketone and dichloromethane was also much lower for the BODA- and MBODA-cured specimens than for those cured with other monoanhydrides.

The mixture of epoxy resin with MBODA was a low-viscosity liquid at room temperature. Although the mixtures of BODA with the resin were pastes at room temperature, they become low-viscosity liquids at slightly elevated temperatures (in the 50° C. range). The temperature at which the first of these mixtures had dropped in viscosity to 1Pa.s was 53° C., compared to 68° C. for the mixture with the commercial dianhydride Epiclon B-4400. Dianhydrides such as BTDA and pyromellitic dianhydride, which yield similar Tg and other physical properties with the epoxy resin to those obtained with BODA, MBODA or Epiclon B-4400, have to be heated to temperatures well above 120° C. to dissolve the anhydride in the epoxy, and pot life at these temperatures is very short (as was shown by the inability to prepare a casting with BTDA under the conditions used in this example).

TABLE 2

| | Cured Properties of Anhydride-Cured Epoxy Resins | | | | | | | | |
|---|---|---|---|---|---|---|---|---|---|
| Experiment # | 1 | 2 | 3 | 4 (control) | 5 (control) | 6 (control) | 7 (control) | 8 (control) | 9 (control) |
| Composition: | | | | | | | | | |
| EPON ® Resin 828, grams | 45.0 | 45.0 | 45.0 | 45.0 | 45.0 | 45.0 | 45.0 | 56.1 | 56.1 |
| BODA, grams | 38.59 | 38.59 | | | | | | | |
| MBODA, grams | | | 41.63 | | | | | | |
| MTHPA, grams | | | | 36.0 | 36.0 | | | | |
| NMA (96%), grams | | | | | | | | | |
| Epiclon B-4400, grams | | | | | | 40.5 | 40.5 | | |
| BTDA, grams | | | | | | | | 35.64 | 43.50 |
| EMI-24 grams | 0.2265 | | | 0.2273 | | 0.2267 | | | |
| DABCO T-45, grams | | 0.4560 | 0.4513 | | 0.4573 | | 0.4582 | 0.5623 | 0.5723 |
| Phenothiazine, grams | 0.1015 | 0.1031 | 0.1062 | 0.1054 | 0.1009 | 0.1012 | 0.1031 | 0.1268 | 0.1268 |
| Monsanto PC-1344 defoamer, grams | 0.2026 | 0.2043 | 0.20 | 0.2054 | 0.2038 | 0.2057 | 0.2022 | 0.25 | 0.25 |
| Anhydride/epoxy ratio, eq/eq$^a$ | 0.90 | 0.90 | 0.90 | 0.90 | 0.90 | 0.907 | 0.907 | 0.90 | 0.90 |
| Uncured properties: | | | | | | | | | |
| Gel time, | | | | | | | | | |
| 150° C., sec. | | | | 298 | 1015 | 465 | | | |
| 180° C., sec. | 55 | 270 | 280 | 83 | 280 | 160 | >1000 | | |
| 25° C. Ubbelohde kinematic viscosity, mm$^2$/s | (paste) | (paste) | 1970 | 1130 | 1100 | 2020 | 1670 | (paste) | (paste) |
| Temp., °C., at which viscosity is 1 Pa · s | 53 | | | | | | | 68 | |
| Cured properties: | | | | | | | | | |
| Rheometrics tan δ peak, °C. | >347 | >356 | >371 | 142 | 154 | 205 | 194 | >350 | |
| R.T. dry flexural (ASTM D-790): | | | | | | | | | |
| Yield/break (y/b) strength, MPa | 55 ± 9 (b) | 52 ± 21 (b) | 47 ± 21 (b) | 131 ± 1 (y) | 126 ± 1 (y) | 127 ± 2 (y) | 114 ± 14 (y) | 40 ± 4 (b) | |
| Tangent modulus, GPa | 2.87 ± 0.10 | 2.95 ± 0.04 | 2.92 ± 0.02 | 3.21 ± 0.01 | 2.99 ± 0.02 | 2.92 ± 0.09 | 2.88 ± 0.06 | 3.13 ± 0.04 | |
| Break elongation, % | 2.0 ± 0.4 | 1.9 ± 0.9 | 1.7 ± 0.8 | >6 | >6 | >6 | >6 | 1.3 ± 0.2 | |
| 93° C. wet flexural (ASTM D-790): | | | | | | | | | |
| Break strength, MPa | 37 ± 5 | 31 ± 17 | 30 ± 9 | 71 ± 1 | 70 ± 1 | 85 ± 1 | 80 ± 1 | 31 ± 13 | |
| Tangent modulus, GPa | 2.19 ± 0.08 | 2.37 ± 0.14 | 2.25 ± 0.01 | 2.53 ± 0.03 | 2.48 ± 0.04 | 2.50 ± 0.01 | 2.42 ± 0.01 | 2.29 ± 0.03 | |
| Break elongation, % | 1.8 ± 0.3 | 1.4 ± 0.9 | 1.4 ± 0.4 | 3.7 ± 0.1 | 3.8 ± 0.2 | 5.4 ± 0.5 | 5.2 ± 0.1 | 1.4 ± 0.6 | |
| Compact tension fracture toughness, Kg MPa-m$^{\frac{1}{2}}$ (ASTM E 399-83) | 0.35 | 0.33 ± 0.01 | (broke) | 0.52 ± 0.02 | 0.52 ± 0.02 | 0.51 ± 0.04 | 0.49 ± 0.01 | (too brittle to test) | |
| Dielectric constant, 1 MHz (ASTM D229/15) | 2.91 | 3.23 | (broke) | 3.10 | 3.10 | 3.14 | 3.16 | 3.41 | |
| Dissipation factor, 1 MHz (ASTM D229/15) | 0.0197 | 0.0208 | (broke) | 0.0202 | 0.0197 | 0.0210 | 0.0197 | 0.0273 | |
| 93° C. H$_2$O pickup, %: | | | | | | | | | |
| 1 day | 1.77 | 1.81 | 1.13 | 0.82 | 1.77 | 0.83 | 0.82 | 1.53 | |
| 2 weeks | 2.06 | 2.03 | 1.43 | 1.11 | 2.06 | 1.00 | 1.00 | 2.05 | |
| Room temp. methyl ethyl ketone pickup, %: | | | | | | | | | |
| 1 day | 0 | 0 | 0 | 0.19 | 0.54 | 0.61 | 0.66 | 0 | |
| 2 weeks | 0.06 | 0.01 | 0 | 2.23 | 6.08 | 6.30 | 6.50 | 0 | |
| Room temp. CH$_2$Cl$_2$ pickup, %: | | | | | | | | | |
| 1 day | 2.65 | 2.60 | 2.58 | disint. | disint. | 32.2 | disint. | 0.73 | |

TABLE 2-continued

| | Cured Properties of Anhydride-Cured Epoxy Resins | | | | | | | | |
|---|---|---|---|---|---|---|---|---|---|
| Experiment # | 1 | 2 | 3 | 4 (control) | 5 (control) | 6 (control) | 7 (control) | 8 (control) | 9 (control) |
| 2 weeks | 16.3 | 15.1 | 20.9 | disint. | disint. | disint. | disint. | 3.79 | |

*Based on actual anhydride content (96% in case of NMA).

EXAMPLE 5

Use of Mixtures of BODA or MBODA with NMA or MTHPA as Epoxy Curing Agents. Five mixtures (mixtures 1–5 in Table 3 below) were prepared as follows. To 250-mL filtering flasks were added the amounts shown of EPON® Resin 828, BODA, MBODA, NMA, MTHPA, Air Products DABCO T-45, phenothiazine, and Monsanto PC-1344 as in Example 4. The flasks were lowered into a 120° C. oil bath and the mixtures were stirred until all the BODA or MBODA had melted and the mixtures were homogeneous. After homogeneous mixtures were obtained, the mixtures were degassed under vacuum, with stirring by a magnetic stirring bar, until bubbling stopped. They were then poured into glass (mixtures #1, 3, 4, 5, 8, 9) or stainless steel (mixtures #2, 6, 7) molds of the same type used in Example 4 and cured by the same cure schedule used in Example 4. Cured properties of the castings are shown in Table 3.

One can see from Table 3 that the cured properties of the epoxy resin cured with BODA/NMA and MBODA/NMA mixtures were intermediate between those of the resins cured with the pure anhydrides (experiments #1, #2 and #8). Noteworthy, however, is the fact that the cured epoxy had a Tg of 255° C. when even 25% of the NMA was replaced by BODA (experiment #5). Corresponding Tg for 25% replacement of NMA by MBODA was 246° C. (experiment #6). This compares with a Tg of 194° C. when the resin was cured with NMA alone (experiment #8). Corresponding Tg's when MTHPA was used instead of NMA were, of course, lower (experiments #7 and #9).

When BODA was used as the sole curing agent (experiment #1), BODA apparently tended to crystallize from the uncured mixture when the uncured mixture was stored at room temperature for approximately one day. (MBODA, as in experiment #2, did not exhibit this behavior.) Dilution of the BODA with NMA yielded resin/curing agent mixtures which remained liquid at room temperature for more than three weeks.

TABLE 3

| | Properties of Anhydride-Cured Epoxy Resins | | | | | | | | |
|---|---|---|---|---|---|---|---|---|---|
| Experiment # | 1 | 2 | 3 | 4 | 5 | 6 | 7 | 8 | 9 |
| Composition: | | | | | | | | | |
| EPON ® Resin 828, grams | 45.0 | 45.0 | 45.0 | 45.0 | 45.0 | 45.0 | 45.0 | 45.0 | 45.0 |
| BODA, grams | 38.59 | | 28.94 | 19.30 | 9.65 | | | | |
| MBODA, grams | | 41.63 | | | | 10.41 | 10.41 | | |
| MTHPA, grams | | | | | | | 27.0 | | 36.0 |
| NMA (96%), grams | | | 10.13 | 20.25 | 30.38 | 30.38 | | 40.5 | |
| DABCO T-45, grams | 0.4560 | 0.4513 | 0.4562 | 0.4516 | 0.4598 | 0.4587 | 0.4562 | 0.4582 | 0.4573 |
| Phenothiazine, grams | 0.1031 | 0.1062 | 0.10 | 0.10 | 0.10 | 0.1046 | 0.1052 | 0.1031 | 0.1009 |
| Monsanto PC-1344 defoamer, grams | 0.2043 | 0.20 | 0.20 | 0.20 | 0.20 | 0.20 | 0.2089 | 0.2022 | 0.2038 |
| Mole % BODA/MBODA in anhydride mixture | 100 | 100 | 75 | 50 | 25 | 25 | 25 | 0 | 0 |
| Anhydride/epoxy ratio, eq/eq$^a$ | 0.90 | 0.90 | 0.90 | 0.90 | 0.90 | 0.90 | 0.90 | 0.907 | 0.90 |
| Uncured properties: | | | | | | | | | |
| Gel time, 150° C., sec. | | | 888 | 950 | 1165 | | | | 1015 |
| 180° C., sec. | 270 | 280 | 230 | 257 | 250 | 360 | 270 | >1000 | 280 |
| 25° C. Ubbelohde kinematic viscosity, mm$^2$/s | (paste) | 1970 | | | | 3600 | 1830 | 1670 | 1100 |
| Cured properties: | | | | | | | | | |
| Rheometrics tan δ peak, °C. | >356 | >371 | −320 | −300 | 255 | 246 | 185 | 194 | 154 |
| R.T. dry flexural (ASTM D-790): | | | | | | | | | |
| Yield/break (y/b) strength, MPa | 52 ± 21 (b) | 47 ± 21 (b) | 73 ± 13 (b) | 49 ± 9 (b) | 46 ± 7 (b) | 63 ± 19 (b) | 75 ± 12 (b) | 114 ± 14 (y) | 126 ± 1 (y) |
| Tangent modulus, GPa | 2.95 ± 0.04 | 2.92 ± 0.02 | 2.86 ± 0.04 | 2.91 ± 0.04 | 2.83 ± 0.04 | 2.86 ± 0.04 | 2.99 ± 0.04 | 2.88 ± 0.06 | 2.99 ± 0.02 |
| Break elongation, % | 1.9 ± 0.9 | 1.7 ± 0.8 | 2.9 ± 0.7 | 1.7 ± 0.4 | 1.6 ± 0.3 | 2.3 ± 0.8 | 2.6 ± 0.5 | >6 | >6 |
| 93° C. wet flexural (ASTM D-790): | | | | | | | | | |
| Break strength, MPa | 31 ± 17 | 30 ± 9 | 31 ± 1 | 37 ± 6 | 45 ± 12 | 53 ± 4 | 76 ± 1 | 80 ± 1 | 70 ± 1 |

TABLE 3-continued

| Properties of Anhydride-Cured Epoxy Resins | | | | | | | | | |
|---|---|---|---|---|---|---|---|---|---|
| Experiment # | 1 | 2 | 3 | 4 | 5 | 6 | 7 | 8 | 9 |
| Tangent modulus, GPa | 2.37 ± 0.14 | 2.25 ± 0.01 | 2.31 ± 0.02 | 2.33 ± 0.03 | 2.36 ± 0.01 | 2.35 ± 0.03 | 2.33 ± 0.01 | 2.42 ± 0.01 | 2.48 ± 0.04 |
| Break elongation, % | 1.4 ± 0.9 | 1.4 ± 0.4 | 1.3 ± 0.1 | 1.6 ± 0.3 | 2.0 ± 0.6 | 2.4 ± 0.2 | 5.8 ± 0.1 | 5.2 ± 0.1 | 3.8 ± 0.2 |
| Compact tension fracture toughness, Kg, MPa-m$^{\frac{1}{2}}$ (ASTM E 399-83) | 0.33 ± 0.01 | (broke) | 0.35 | 0.37 ± 0.01 | 0.41 ± 0.01 | 0.40 ± 0.01 | 0.53 ± 0.03 | 0.49 ± 0.01 | 0.52 ± 0.02 |
| Dielectric constant, 1 MHz (ASTM D229/15) | 3.23 | (broke) | 3.20 | 3.22 | 3.17 | 3.23 | 3.24 | 3.16 | 3.10 |
| Dissipation factor, 1 MHz (ASTM D229/15) | 0.0208 | (broke) | 0.0202 | 0.0208 | 0.0221 | 0.0222 | 0.0225 | 0.0197 | 0.0197 |
| 93° C. H$_2$O pickup, %: | | | | | | | | | |
| 1 day | 1.81 | 1.13 | 1.42 | 1.18 | 1.05 | 0.77 | 0.68 | 0.82 | 1.77 |
| 2 weeks | 2.03 | 1.43 | 1.80 | 1.51 | 1.32 | 1.01 | 0.90 | 1.00 | 2.06 |
| Room temp. methyl ethyl ketone pickup, %: | | | | | | | | | |
| 1 day | 0 | 0 | 0 | 0 | 0 | 0 | 0 | 0.66 | 0.54 |
| 2 weeks | 0.01 | 0 | 0 | 0.25 | 0.59 | 0.15 | 1.63 | 6.50 | 6.08 |
| Room temp. CH$_2$Cl$_2$ pickup, %: | | | | | | | | | |
| 1 day | 2.60 | 2.58 | 2.38 | 3.36 | 7.33 | 7.87 | 22.1 | disint. | disint. |
| 2 weeks | 15.1 | 20.9 | 20.6 | 33.5 | disint. | 43.2 | disint. | disint. | disint. |

$^a$Based on actual anhydride content 96% in case of NMA).

EXAMPLE 6

Copolymerization of Epoxy/BODA with Bismaleimide/1,2-Dimethylenecyclobutane (DMCB) Mixtures. Six mixtures (mixtures 1-6 in Table 4 below) were prepared as follows. In mixtures #2 and #3, enough COMPIMIDE® MDAB (the bismaleimide of 4,4'-methylenedianiline) was added to the basic BODA-EPON Resin 828 formulation (mixture #1) to insert an MDAB unit between half (mixture #2) or all (mixture #3) of the pairs of BODA units used. In mixtures #4 and #5, sufficient MDAB to give chain lengths of more than one MDAB unit between BODA units was used, with a stoichiometric amount of DMCB added to link the excess maleimide end groups together with one DMCB unit between each pair of MDAB units. An amount of bismaleimide sufficient to give an average chain length of 3 (mixture #4) or 9 (mixture #5) MDAB units between each pair of BODA units was used. Mixture #6 was a control mixture of 1 mole of DMCB per mole of bismaleimide, containing no epoxy or BODA. In the preparation of the mixtures containing DMCB (mixtures #4, 5 and 6), to 500-mL glass bottles were added the amounts shown of bismaleimide, a distilled dimethylenecyclobutane (DMCB) fraction containing mostly 1,2-isomer, phenothiazine (to inhibit radical polymerization of the diene and maleimide groups) and Monsanto PC-1344 defoamer (an acrylic oligomer, added to prevent excessive foaming during vacuum degassing and to enable the preparation of void-free castings) along with 180 grams of dichloromethane as solvent. The bottles were placed on rollers and rolled overnight (or longer) at room temperature to allow completion of the first-stage Dieis-Alder reaction between the 1,2-dimethylenecyclobutane and the maleimide groups of the bismaleimide. The BODA, epoxy resin and DABCO T-45 were added to the mixtures at this point and mixed until homogeneous.

The mixtures were then poured into 250-mL Erlenmeyer flasks with a vacuum connection. The flasks were then placed in a 120° C. oil bath and the contents were swirled as solvent, 1,3-dimethylenecyclobutane, and other volatile unreacted materials were removed, first at atmospheric pressure and then under mechanical pump vacuum for a few minutes until bubbling had essentially stopped.

In the preparation of mixtures containing no DMCB (mixtures #1, 2 and 3), to 250-mL filtering flasks were added the amounts shown of epoxy resin, BODA, bismaleimide, DABCO T-45, phenothiazine, and Monsanto PC-1344 as in Example 4. The flasks were lowered into a 120° C. oil bath and the mixtures were stirred until all the BODA had melted and the mixtures were homogeneous. After homogeneous mixtures were obtained, the mixtures were degassed under vacuum, with stirring by a magnetic stirring bar, until bubbling stopped.

The degassed molten mixtures were then poured into the stainless steel molds used in Example 4 and cured under 750 kPa nitrogen pressure by the same cure schedule used in Example 4. A few grams of each uncured sample were kept as a retain for characterization of uncured properties. Cured properties of the castings are shown in Table 4.

One can see from Table 4 that the toughness of the system increased strongly with increasing amounts of bismaleimide and DMCB used (and increasing bismaleimide-DMCB chain length between epoxy-BODA crosslinks), at relatively little cost to Tg. Along with fracture toughness, other toughness-related properties such as flexural strength and elongation were also increased by lengthening the BMI-DMCB linkages. Uncured viscosity of the blends was higher than that of the epoxy-BODA mixture (experiment #1) but lower than that of the DMCB-BMI mixture containing no epoxy (experiment #6).

TABLE 4

| | Epoxy/BODA Cocured With BMI/DMCB | | | | | |
|---|---|---|---|---|---|---|
| Experiment # | 1 | 2 | 3 | 4 | 5 | 6 |
| Composition: | | | | | | |
| EPON ® Resin 828, grams | 45.0 | 45.0 | 45.0 | 22.86 | 9.35 | |
| epoxy equivalents | 0.24 | 0.24 | 0.24 | 0.1222 | 0.05 | |
| BODA, grams | 38.59 | 38.59 | 38.59 | 19.60 | 8.02 | |
| moles | 0.2166 | 0.2166 | 0.2166 | 0.1100 | 0.0450 | |
| DABCO T-45, grams | 0.4560 | 0.4522 | 0.4519 | 0.23 | 0.09 | |
| COMPIMIDE ® MDAB, grams | | 19.40 | 38.81 | 59.13 | 72.56 | 73.10 |
| moles | | 0.0541 | 0.1083 | 0.1650 | 0.2025 | 0.2040 |
| 1,2-Dimethylenecyclobutane (DMCB): | | | | | | |
| Crude distillate, grams | | | | 9.19 | 15.05 | 19.78 |
| % 1,2-isomer in crude distillate (GC area) | | | | 95.863 | 95.863 | 82.606 |
| Net 1,2-isomer, grams | | | | 8.81 | 14.43 | 16.34 |
| moles | | | | 0.11 | 0.18 | 0.2039 |
| Phenothiazine, grams | 0.1031 | 0.10 | 0.10 | 0.20 | 0.20 | 0.21 |
| Monsanto PC-1344 defoamer, grams | 0.2043 | 0.20 | 0.20 | 0.20 | 0.20 | 0.24 |
| Anhydride/epoxy ratio, eq/eq$^a$ | 0.90 | 0.90 | 0.90 | 0.90 | 0.90 | |
| Average number of COMPIMIDE MDAB units between each pair of BODA units | 0 | 0.5 | 1 | 3 | 9 | |
| Uncured properties: | | | | | | |
| Temp., °C., at which viscosity is 1 Pa · s | 53 | 58 | 65 | 85 | 107 | 125 |
| Cured properties: | >356 | 340 | 335 | 316 | 285 | 291 |
| Rheometrics tan δ peak, °C. | | | | | | |
| R.T. dry flexural (ASTM D-790): | | | | | | |
| Yield/break (y/b) strength, MPa | 52 ± 21 (b) | 54 ± 15 (b) | 70 ± 9 (b) | 92 ± 29 (b) | 126 ± 1 (y) | 122 ± 1 (y) |
| Tangent modulus, GPa | 2.95 ± 0.04 | 2.95 ± 0.01 | 2.89 ± 0.02 | 2.93 ± 0.03 | 2.86 ± 0.02 | 2.67 ± 0.02 |
| Break elongation, % | 1.9 ± 0.9 | 1.9 ± 0.6 | 2.7 ± 0.5 | 4.2 ± 2.0 | ≧6.5 | ≧6.5 |
| 93° C. wet flexural (ASTM D-790): | | | | | | |
| Yield/break (y/b) strength, MPa | 31 ± 17 (b) | 40 ± 9 (b) | 61 ± 8 (b) | 67 ± 4 (b) | 80 ± 2 (y) | 81 ± 1 (y) |
| Tangent modulus, GPa | 2.37 ± 0.14 | 2.28 ± 0.04 | 2.23 ± 0.03 | 2.34 ± 0.06 | 2.35 ± 0.07 | 2.33 ± 0.02 |
| Break elongation, % | 1.4 ± 0.9 | 1.8 ± 0.5 | 3.3 ± 0.7 | 3.8 ± 0.4 | ≧6.2 | ≧6.5 |
| Compact tension fracture toughness, Kq, MPa-m$^{\frac{1}{2}}$ (ASTM E 399-83) | 0.33 ± 0.01 | 0.44 | 0.53 ± 0.05 | 0.79 | 1.29 ± 0.12 | 2.93 ± 0.13 |
| Dielectric constant, 1 MHz (ASTM D229/15) | 3.23 | 3.35 | 3.44 | 3.63 | 3.55 | 3.40 |
| Dissipation factor, 1 MHz (ASTM D229/15) | 0.0208 | 0.0214 | 0.0222 | 0.0206 | 0.0174 | 0.0156 |
| 93° C. H$_2$O pickup, %: | | | | | | |
| 1 day | 1.81 | 2.04 | 2.55 | 2.08 | 1.71 | 1.66 |
| 2 weeks | 2.03 | 2.64 | 3.33 | 2.79 | 2.49 | 2.28 |
| Room temp. methyl ethyl ketone pickup, %: | | | | | | |
| 1 day | 0 | 0 | 0 | 0.05 | 0.03 | 0 |
| 2 weeks | 0.01 | 0 | 0.37 | 1.00 | 0.78 | 1.69 |
| Room temp. CH$_2$Cl$_2$ pickup, %: | | | | | | |
| 1 day | 2.60 | 3.06 | 4.77 | 14.4 | 61.7 | 169 |
| 2 weeks | 15.1 | 27.7 | 45.1 | 53.6 | disint. | 179 |

I claim:

1. A composition comprising:
   (a) an epoxy resin; and
   (b) an anhydride-functional compound of the formula

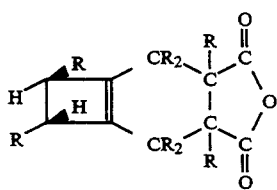

in which each R is selected independently from the group consisting of hydrogen, C$_{1-10}$ alkyl, aryl, halide and C$_{1-10}$ hetero-interrupted (alkyl or aryl).

2. The composition of claim 1 in which each R is independently selected from hydrogen or methyl.

3. The composition of claim 1 in which the anhydride-functional compound is bicyclo[4.2.0]oct-1(6)-ene-3,4-dicarboxylic anhydride.

4. The composition of claim 1 in which the anhydride-functional compound is 3-methylbicyclo[4.2.0]oct-1(6)-ene-3,4-dicarboxylic anhydride.

5. The composition of claim 1 in which the anhydride-functional compound is present in the composition in an amount within the range of about 0.5 to about 1.2 moles per mole of epoxy resin.

6. The composition of claim 1 in which the epoxy resin is a diglycidyl ether of bisphenol A or bisphenol F.

7. The composition of claim 1 which further comprises at least one of methyl tetrahydrophthalic anhydride, nadic methyl anhydride, a piperylene/maleic anhydride adduct or benzophenonetetracarboxylic dianhydride.

8. The composition of claim 1 which further comprises a bismaleimide resin.

9. The composition of claim 8 which further comprises a 1,2-dialkylidenecyclobutane.

10. The composition of claim 9 in which the 1,2-dialkylidenecyclobutane is 1,2-dimethylenecyclobutane.

11. The composition of claim 1 which further comprises phenothiazine.

* * * * *